(12) United States Patent
Osypka

(10) Patent No.: US 9,138,575 B2
(45) Date of Patent: Sep. 22, 2015

(54) BALLOON CATHETER

(71) Applicant: Peter Osypka Stiftung, Grenzach-Wyhlen (DE)

(72) Inventor: Peter Osypka, Grenzach-Wyhlen (DE)

(73) Assignee: Peter Osypka Stiftung, Grenzach-Wyhlen (DE)

(*) Notice: Subject to any disclaimer, the term of this patent is extended or adjusted under 35 U.S.C. 154(b) by 0 days.

(21) Appl. No.: 14/352,149

(22) PCT Filed: Oct. 8, 2012

(86) PCT No.: PCT/DE2012/000980
§ 371 (c)(1),
(2) Date: Apr. 16, 2014

(87) PCT Pub. No.: WO2013/064132
PCT Pub. Date: May 10, 2013

(65) Prior Publication Data
US 2014/0277319 A1    Sep. 18, 2014

(30) Foreign Application Priority Data
Nov. 5, 2011 (DE) .................... 20 2011 107 537 U

(51) Int. Cl.
*A61N 1/05* (2006.01)
*A61M 25/10* (2013.01)
*A61B 5/01* (2006.01)
*A61B 5/00* (2006.01)

(52) U.S. Cl.
CPC .......... *A61N 1/0517* (2013.01); *A61M 25/1002* (2013.01); *A61B 5/01* (2013.01); *A61B 5/6853* (2013.01); *A61M 2025/1015* (2013.01); *A61M 2210/105* (2013.01); *A61N 1/0563* (2013.01)

(58) Field of Classification Search
CPC ....................................................... A61N 1/05
USPC ................................................. 607/116, 124
See application file for complete search history.

(56) References Cited

U.S. PATENT DOCUMENTS

| 4,706,688 | A | | 11/1987 | Don Michael et al. | |
|---|---|---|---|---|---|
| 5,056,532 | A | * | 10/1991 | Hull et al. ...................... | 607/124 |
| 2002/0161421 | A1 | * | 10/2002 | Lee et al. ....................... | 607/116 |
| 2003/0097082 | A1 | * | 5/2003 | Purdy et al. .................... | 600/594 |
| 2013/0289682 | A1 | * | 10/2013 | Barman et al. ................. | 607/116 |

FOREIGN PATENT DOCUMENTS

| DE | 19626181 A1 | 1/1998 |
|---|---|---|
| WO | WO-9509015 A2 | 4/1995 |

OTHER PUBLICATIONS

PCT International Search Report dated Jun. 18, 2013 issued on the corresponding PCT International Application No. PCT/DE2012/000980 filed Oct. 8, 2012.

* cited by examiner

*Primary Examiner* — Nicole F Lavert
*Assistant Examiner* — Nadia A Mahmood
(74) *Attorney, Agent, or Firm* — Locke Lord LLP; Scott D. Wofsy; Daniel J. Fiorello

(57) ABSTRACT

The invention relates to a multi-pole esophageal electrode catheter that can be used for monitoring, pacing, and cardioversion of atrial fibrillation of the heart, the catheter having a flexible shaft (15) having a proximal end and a distal end and a multipolar electrode (3), characterized in that the distal end of the catheter is formed as a side arranged inflatable balloon (4) so that the multi-pole electrode (3) is aligned in the direction of the heart wall is constantly by means of the balloon.

10 Claims, 4 Drawing Sheets

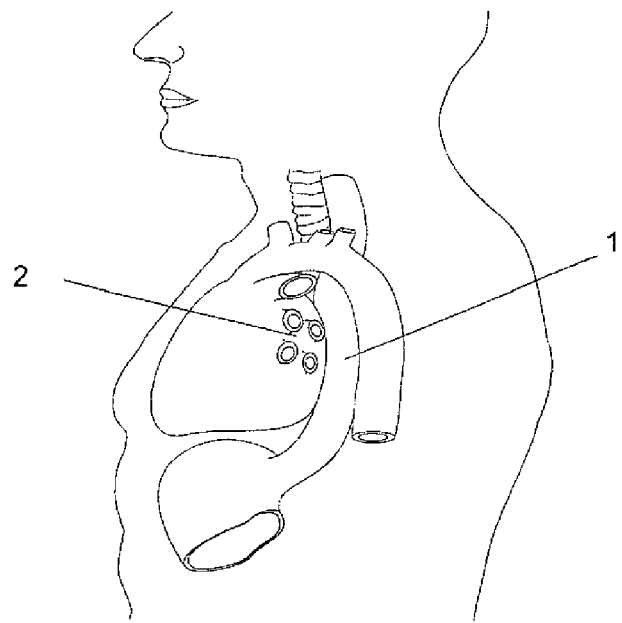
Fig. 1
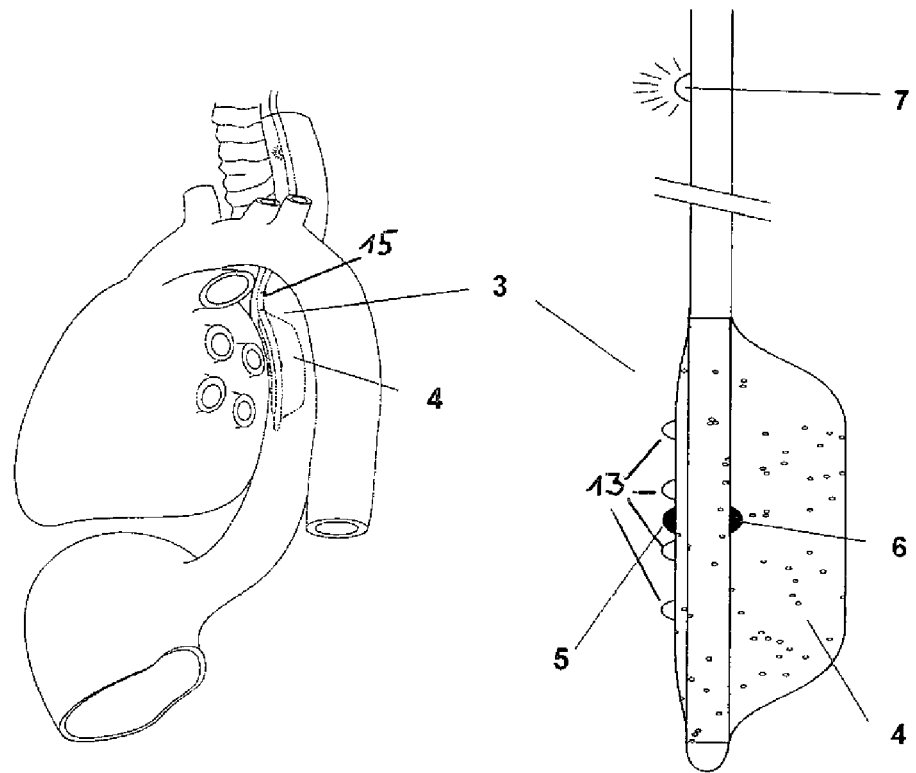
Fig. 2a
Fig. 2b

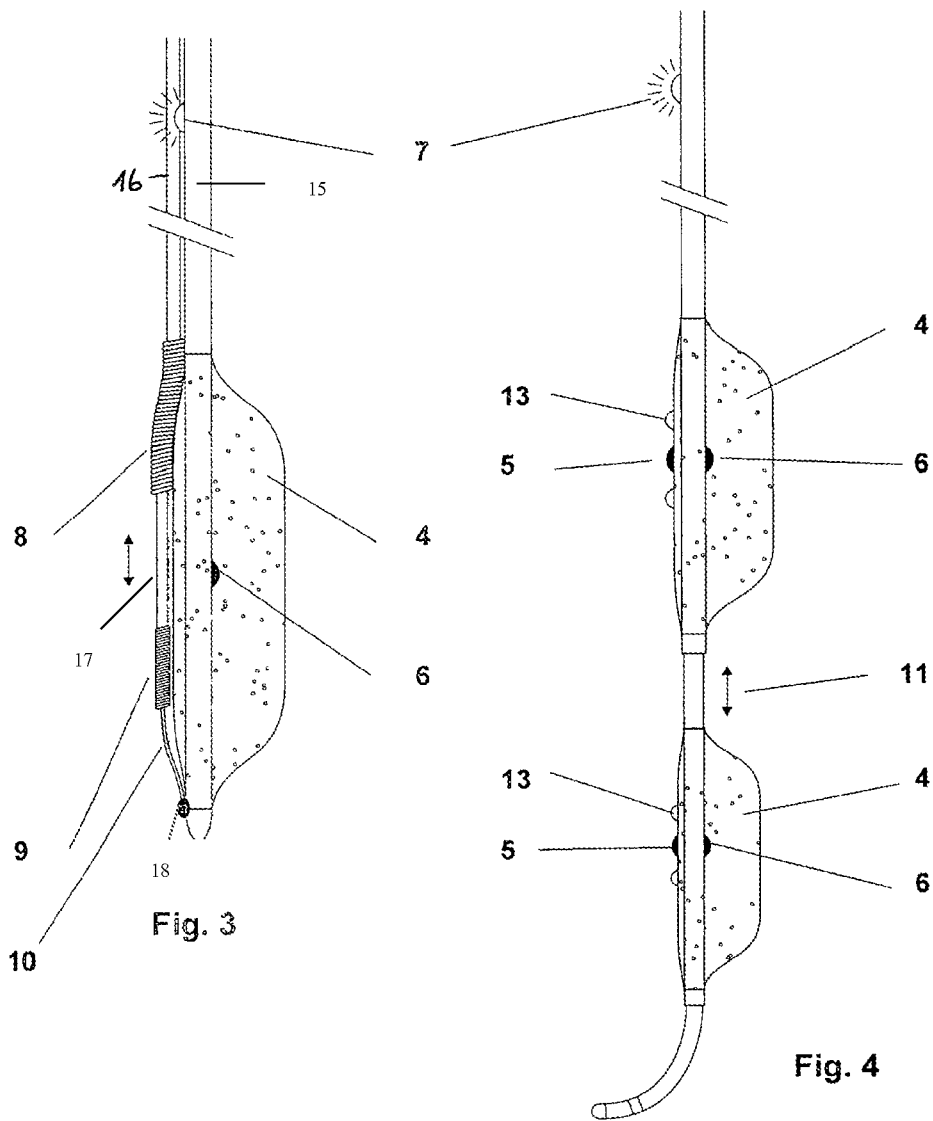

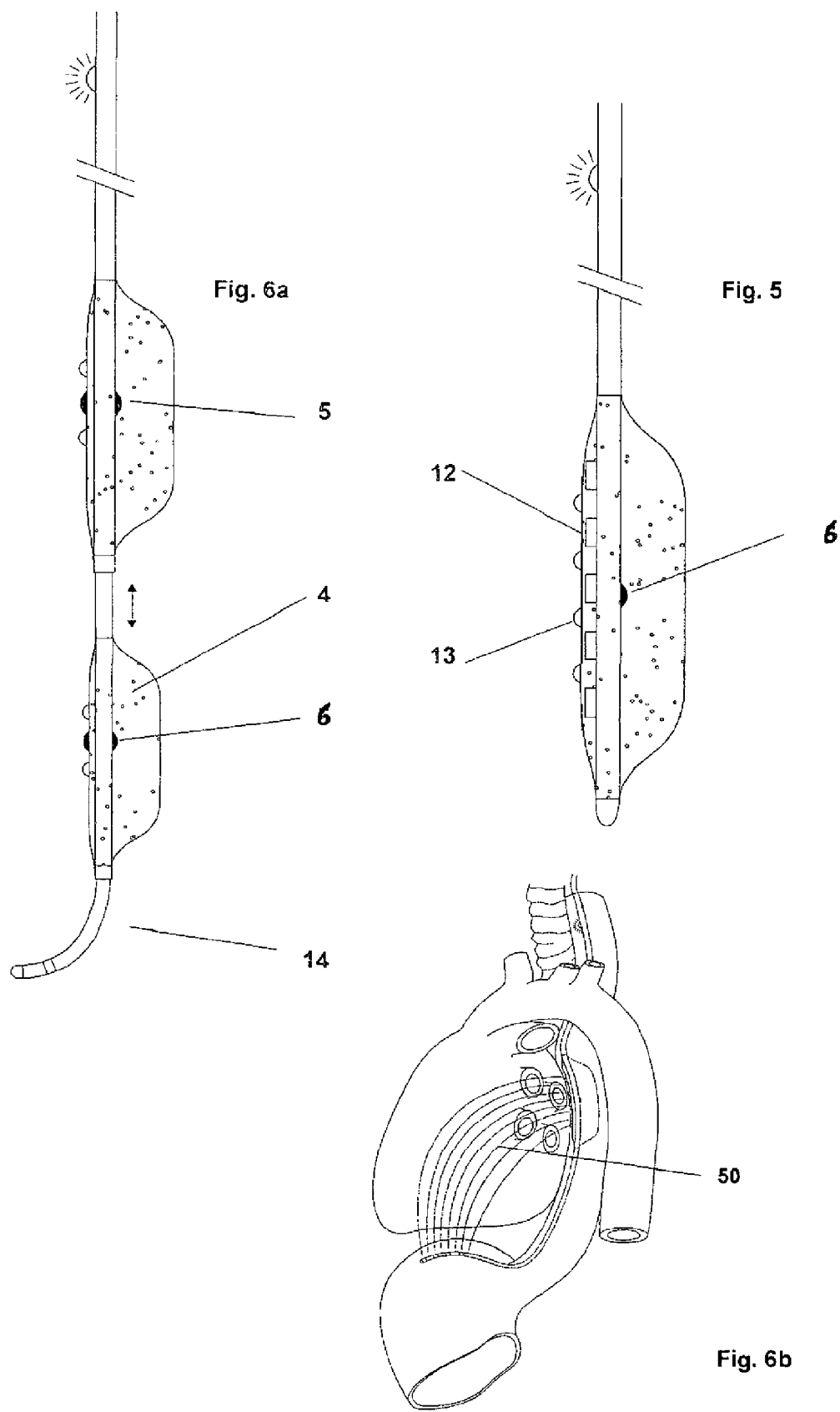

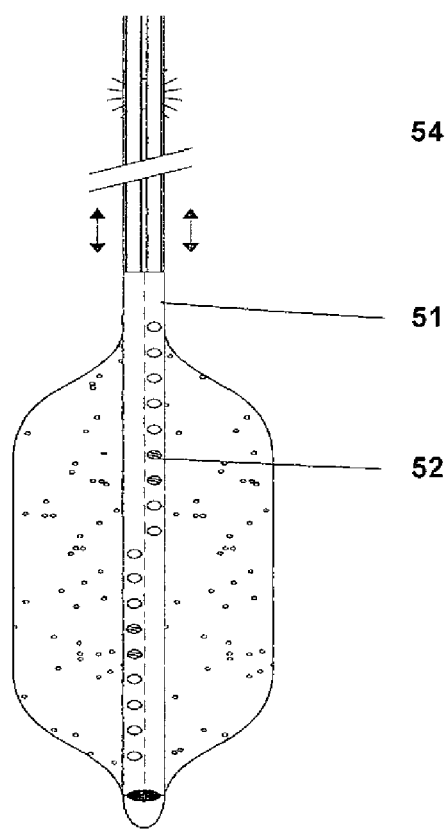
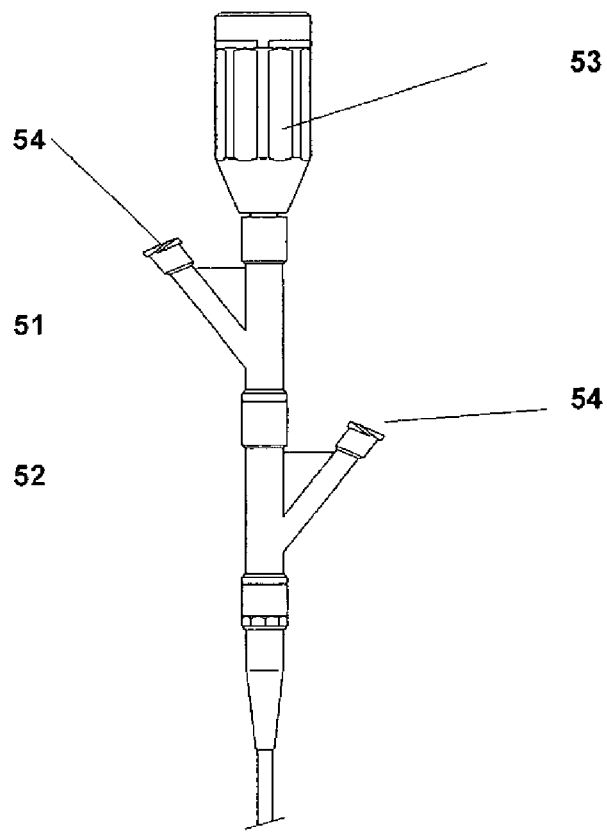
Fig. 7
Fig. 8
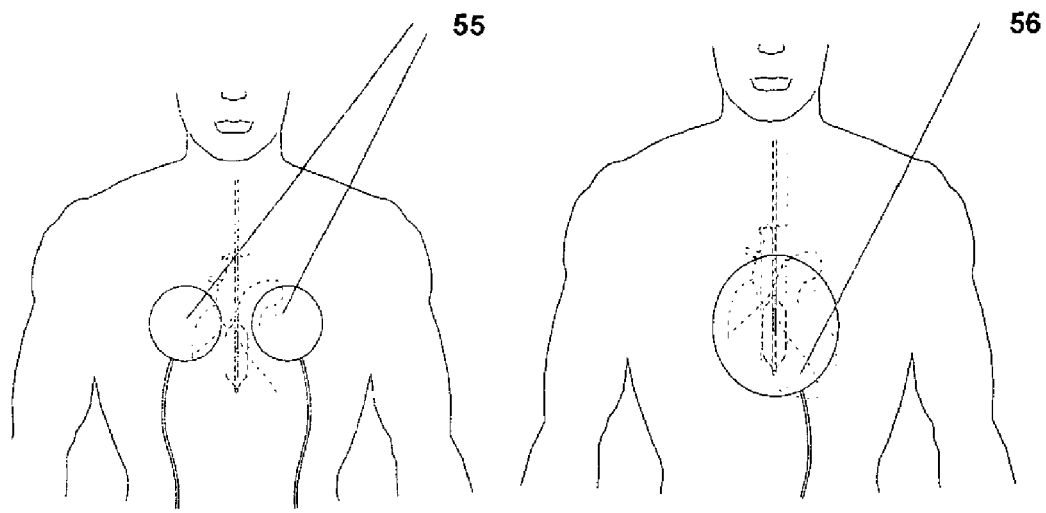
Fig. 9
Fig. 10

BALLOON CATHETER

CROSS-REFERENCE TO RELATED APPLICATIONS

This application is the national phase under 35 U.S.C. §371 of PCT International Application No. PCT/DE2012/000980, filed Oct. 8, 2012, which claims priority to German Application No. 20 2011 107 537.4, filed Nov. 5, 2011, the entire contents of each of the aforementioned applications being incorporated herein by reference.

FIELD OF THE DISCLOSURE

The invention relates to an oesophageal balloon catheter device which can be used to treat atrial fibrillation by stimulation or cardioversion and which can be used for defibrillation of the heart.

BACKGROUND

Post-operative atrial fibrillation occurs relatively frequently and is one of the main reasons for post-operative morbidity. Post-operative atrial fibrillation seems to have increased in the last few years due to the fact that patients are getting ever older. There are clinical reports showing that 30%-40% of patients suffer from atrial fibrillation after coronary artery bypass surgery. Atrial fibrillation is an irregular heart rhythm whereby many impulses begin simultaneously and spread through the atria causing a rapid and disorganized heartbeat and acute haemodynamic instability. Electrical cardioversion is a known procedure in which the electric current is used to reset the heart's rhythm back to its regular pattern. Cardioversion requires a short acting anesthesia which can exacerbate existing neuronal problems (vigilance) occurring in patients after a bypass operation, as a result of the heart operation they have just come through; this can lead to delayed awakening or even a need for further intubation with mechanical ventilation. Furthermore atrial fibrillation increases the risk of stroke. If the rhythm disorder persists for longer than 24 hours, anticoagulation therapy becomes necessary in order to reduce the formation of thrombi and the risk of a stroke. All these factors lead after a bypass operation to complicated post-operative healing which is reflected in increased costs due to an extended stay of the patients in hospital of about 5 days. Treating atrial fibrillation it is of great importance that the electrical shock is applied as quickly as possible. That currently happens by applying large-surface electrodes on the surface of the chest over the heart. The shock energy is between 200 and 300 Joules.

Electrodes for temporary stimulation of the heart via the oesophagus have been known for many years and they are used routinely. The treatment of atrial or ventricular fibrillation occurring after a cardiac surgery or due to another heart disease is currently performed by an external electrical energy impulse using a defibrillator, applied by placing or adhering large surface electrodes on the patient's chest. Before treatment of atrial fibrillation an ultrasound examination of the left atrial appendage is required. Furthermore anaesthesia is necessary during cardioversion. These treatments lengthen the patient's stay on the intensive care unit by about 2-4 days. During cardio-resynchronisation therapy (CRT), the setting of the impulse delay between the two ventricle stimulation impulses is of great importance for optimum adjustment of cardiac output. Oesophageal electrodes are of great help hereby as well. Using electrodes in the oesophagus, it is important that the electrodes lie as close to the heart as possible. The optimal positioning or alignment of the oesophageal catheter is often very difficult and requires x-ray. When treating atrial fibrillation using RF ablation, cooling of the oesophagus would be desirable.

There is a need to provide an oesophageal catheter whereby the electrodes lie as close to the heart as possible, particularly close to the left atrium, allowing immediate, rapid and easily accessible use and optimal positioning of the oesophageal catheter for various diagnostic and therapeutic approaches for the treatment of heart problems. The oesophageal catheter itself is suitable for the treatment of heart problems as the oesophagus runs anatomically directly behind the left atrium and parts of the ventricle and the catheter can be introduced simply by swallowing without anaesthetic.

SUMMARY

A multi-pole oesophageal electrode catheter device which can be used for monitoring, stimulation and cardioversion of the heart, when treating atrial fibrillation of the heart, whereby the catheter includes a flexible shaft with a proximal end and a distal end and a multi-pole electrode whereby the distal end of the catheter is formed as an inflatable balloon arranged on one side so that the multi-pole electrode is aligned appropriately in the direction of the heart with the aid of the balloon.

The balloon can be filled with gas and/or a liquid. The liquid can be a coolant.

The catheter can include two inflatable balloons, whereby a multi-pole electrode is arranged on each balloon. The distance between each of the balloons can be changed.

The shaft can include a hollow channel through which another catheter can be introduced.

The catheter can include at least one temperature sensor which measures the temperature in the oesophagus and optionally comprises another temperature sensor.

The catheter can include at least one magnet on the side turned to the heart.

The poles of the multi-pole electrode can be arranged on two channels isolated from each other, whereby the channels are provided with small openings and whereby the channels can be moved against each other. The poles of the electrodes can be formed as coils.

The catheter can further include a shaft bearing the proximal pole of the electrode, while the distal pole inside the shaft is arranged so that it can be adjusted via a guide wire.

At least one light diode can be applied on the shaft running parallel in the same electrode plane.

BRIEF DESCRIPTION OF THE DRAWINGS

Further details, characteristics and benefits of the invention can be found in the following part of the description, where the drawings explain the invention in more detail.

FIG. 1 shows the anatomical position of the heart and oesophagus in the human body.

FIG. 2 shows a multi-pole oesophageal electrode catheter device for cardioversion and stimulation of the heart, wherein the electrodes can be aligned appropriately in the direction of the heart with the aid of the balloon.

FIG. 3 shows a bipolar oesophageal electrode catheter device for cardioversion and stimulation of the heart having a balloon and wherein the distance between the poles can be changed.

FIG. 4 shows a multi-pole oesophageal electrode catheter device for cardioversion and stimulation of the heart consisting of two balloons wherein the distance between the balloons and thus the distance between the poles can be changed and wherein the poles can be appropriately aligned in the direction of the heart.

FIG. 5 shows a multi-pole oesophageal electrode catheter device for cardioversion and stimulation of the heart, wherein the poles have in addition been provided with magnets.

FIG. 6 shows a multi-pole oesophageal electrode catheter device for cardioversion and stimulation of the heart, consisting of one or two balloons as shown in FIG. 4. The catheter comprises at least one hollow channel through which another catheter can be introduced.

FIG. 7 shows a multi-pole oesophageal electrode catheter device for cardioversion and stimulation of the heart having a balloon, wherein the poles run in channels and wherein the distance between the poles can be changed and wherein the electrodes can be aligned appropriately in the direction of the heart with the aid of the balloon.

FIG. 8 shows the proximal part of the oesophageal balloon catheter.

FIG. 9 shows an oesophageal balloon catheter for cardioversion and stimulation of the heart with two additional external electrodes placed over the atria.

FIG. 10 shows an oesophageal balloon catheter for defibrillation and stimulation of the heart with an additional large surface external electrode placed over the ventricles.

DETAILED DESCRIPTION

FIG. 1 shows the anatomical position of the heart and oesophagus in the human body. It is easy to see that the oesophagus (1) lies anatomically close to the left atrium of the heart (2). FIG. 2a shows one embodiment of the multi-pole oesophageal electrode catheter. The catheter comprises a flexible shaft (15) with a proximal end and a distal end and a multi-pole electrode (3) whereby the distal end of the catheter is formed on one side as an inflatable balloon (4) so that the multi-pole electrode (3) is aligned appropriately in the direction of the heart with the aid of the balloon.

FIG. 2b shows the embodiment of FIG. 2a in more detail. You can identify the poles (13) of the multi-pole electrode (3). The balloon (4) can be filled with cold liquid and contains a temperature sensor (6). Another temperature sensor (5) measures the temperature in the oesophagus. A red diode (LED) (7), which is arranged at a defined distance from the balloon and is visible in use from outside in the area of the larynx, is an aid to positioning the balloon. FIG. 3 shows one embodiment of a bipolar oesophageal electrode catheter device for cardioversion and stimulation of the heart having a balloon (4). The poles of the electrode (3) are formed as metal coils (8, 9). The coils can be variously configured in size and clearance depending on the anatomical conditions. The catheter comprises in addition to shaft (15) another shaft (16) with the proximal pole (8) being fixed thereon. The distal pole (9) is movable by means of the guide wire (10) inside shaft (16).

While the proximal pole (8) of the electrode is fixed on the outer shaft (16), the distal pole (9) of the electrode is movable as a separate shaft (17) inside the shaft (16) and the distance between pole (9) and pole (8) can thus be adjusted depending on the patient's anatomical conditions.

The guide wire (10) is distally connected to the catheter shaft (17). A temperature sensor (18) is also attached to the catheter shaft (17). Temperature sensors can be attached to several parts of the catheter, depending on the customer's requirements, such as, for example, inside the balloon or on the outer parts of the balloon. Mechanical fixation of the two pole shafts is carried out after optimum positioning at the proximal end with a screw-on valve (not shown here).

The electrical resistance in the catheter to the electrode poles should be as low as possible. Known biocompatible materials such as stainless steel and its alloys, platinum, gold, silver and tungsten can be used for the coils, optionally with conductive coatings. If the balloon (4) is filled with liquid or gas with the poles aligned in the direction of the heart, the poles are pressed by the balloon against the wall of the oesophagus, placing the poles close to the left atrium, leading to a reduction in the electrical energy required for cardioversion or stimulation. The balloon can also be used with appropriate filling as a cooling device for the oesophagus, e.g. during high-frequency ablation. With integration of the sensors (6), temperature monitoring can also be carried out.

FIG. 4 shows a multi-pole oesophageal electrode catheter device having two separate balloons (4) where the poles (13) are arranged on separate balloons (4). The arrangement of the poles on each balloon can be identically as demonstrated in FIG. 4. However, a different arrangement is conceivable. The distance (11) between the balloons and thus the distance between the poles can be changed. The electrodes are appropriately aligned by the balloon in the direction of the heart. This optimally adjusts the catheter to the anatomical situation. That is especially beneficial if the catheter is to be used for atrial cardioversion or defibrillation. Additional temperature sensors (5, 6) can be attached here as well.

FIG. 5 shows a multi-pole oesophageal electrode catheter device having a balloon for cardioversion and stimulation of the heart which has been additionally provided with magnets (12). The magnets serve to fix in place guide wires which are distally equipped with appropriate magnets and are found in the left atrium. Via these guide wires further catheters can be very easily introduced into the left atrium to eliminate atrial fibrillation, for example appropriate balloon catheters and these balloon catheters can be pressed against the exits from the pulmonary veins in order to realise the desired uniform ablation channels.

FIG. 6a shows a multi pole oesophageal electrode catheter device having two separate balloons (4) for cardioversion and stimulation of the heart as shown in FIG. 4 which comprises at least one hollow channel through which another electrode catheter (14) can be introduced. Such an additional catheter is especially advantageous for defibrillation and should be steerable and is preferably positioned in the stomach below the apex of the heart.

FIG. 6b shows the field strength distribution (50) of the multi-pole electrode catheter device during defibrillation in ventricular fibrillation therapy. Here all areas of the heart are optimally captured by the electric shock.

FIG. 7 shows an oesophageal electrode catheter device where the poles are arranged in two channels (51) isolated from each other, said channels having small openings (52) to give poles (13) free. The distance between the poles (13) can be changed. The poles can be directed appropriately towards the heart by means of the balloon. The pole channels can consist of one or more metal strips, or can be composed of several isolated conductive sheets which are joined together, said sheets are made of metal or of metal coated plastic (e.g. Kapton polyimide) so that the poles can be designed as required in terms of size, shape and clearance. Depending on the application, the poles can be individually arranged on the channels. A number of pole positions can be verified by independently adjusting the channels.

By moving the flexible channels and filling the balloon, each pair of electrodes can be appropriately positioned according to the anatomical condition of the heart. In addition to electrical poles for stimulation, defibrillation or high frequency ablation, such guide channels can also contain sensors for measuring temperature or ultrasound crystals as well as optical measuring instruments. Even the isolated channels where the poles are found can be changed in shape, size and number.

FIG. 8 shows the proximal part of the oesophageal catheter, i.e. the connector (53) with the appropriate number of poles and the necessary introductions (54) for filling the balloon.

FIG. 9 shows an oesophageal electrode catheter for cardioversion and stimulation of the heart with two external electrodes (55) placed over the atria. This arrangement can also be used for treatment of atrial fibrillation. The electric shock is applied between the balloon poles and the two external electrodes (55).

FIG. 10 shows an oesophageal electrode catheter for defibrillation and stimulation of the heart with a large-surface external electrode (56) placed over the ventricles. This arrangement can be used for the treatment of ventricular fibrillation. The electric shock is applied between the poles of the balloon and the external electrode.

While the apparatuses, systems, and methods of the subject disclosure have been shown and described with reference to embodiments, those skilled in the art will readily appreciate that changes and/or modifications may be made thereto without departing from the spirit and scope of the subject disclosure.

The invention claimed is:

1. Multi-pole oesophageal electrode catheter device which can be used for monitoring, stimulation and cardioversion of the heart, when treating atrial fibrillation of the heart, whereby the catheter comprises:
   a flexible shaft with a proximal end and a distal end, whereby the distal end of the catheter is formed to include two inflatable balloons, wherein a multi-pole electrode is arranged on one side of each balloon so that each multi-pole electrode is aligned appropriately in the direction of the heart with the aid of each balloon, and wherein the distance between each of the balloons is adjustable.

2. Catheter device according to claim 1, whereby the balloon is filled with gas and/or a liquid.

3. Catheter device according to claim 2, whereby the liquid is a coolant.

4. Catheter device according to claim 1, whereby the shaft comprises a hollow channel through which another catheter can be introduced.

5. Catheter device according to claim 1 whereby the catheter comprises at least one temperature sensor which measures the temperature in the oesophagus and optionally comprises another temperature sensor.

6. Catheter device according to claim 1, whereby the catheter comprises at least one magnet on the side turned to the heart.

7. Catheter device according to claim 1, whereby the poles of the multi-pole electrode are arranged on two channels isolated from each other, whereby the channels are provided with small openings and whereby the channels can be moved against each other.

8. Catheter device according to claim 1, whereby the poles of the electrodes are formed as coils.

9. Catheter device according to claim 8, whereby the catheter further comprises shaft bearing the proximal pole of the electrode, while the distal pole inside the shaft is arranged so that it can be adjusted via a guide wire.

10. Catheter device according to claim 1, whereby at least one light diode is applied on the shaft running parallel in the same electrode plane.

* * * * *